US006534072B2

(12) United States Patent
Mondet et al.

(10) Patent No.: US 6,534,072 B2
(45) Date of Patent: *Mar. 18, 2003

(54) PROCESS FOR INCREASING THE PERSISTENCE OF AT LEAST ONE COSMETIC EFFECT AND/OR CARE EFFECT OF A COSMETIC COMPOSITION, COSMETIC COMPOSITION AND USE THEREOF

(75) Inventors: Jean Mondet, Aulnay-Sous-Bois (FR); Nathalie Mougin, Paris (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/848,237

(22) Filed: May 4, 2001

(65) Prior Publication Data

US 2001/0053377 A1 Dec. 20, 2001

(30) Foreign Application Priority Data

May 9, 2000 (FR) ............................................. 00 05878

(51) Int. Cl.$^7$ ................................................. A61K 6/00
(52) U.S. Cl. ........................... 424/401; 424/59; 424/63; 424/64; 424/65
(58) Field of Search ........................... 424/401, 59, 63, 424/64, 65; 514/944

(56) References Cited

U.S. PATENT DOCUMENTS

| 4,744,978 A | | 5/1988 | Homan et al. | |
|---|---|---|---|---|
| 5,160,732 A | | 11/1992 | Katsoulis et al. | |
| 5,280,019 A | | 1/1994 | Klimisch | |
| 5,738,841 A | * | 4/1998 | Mellul et al. | 424/59 |
| 5,919,441 A | * | 7/1999 | Mendolia et al. | 424/78.08 |
| 6,051,216 A | * | 4/2000 | Barr et al. | 424/78.35 |

FOREIGN PATENT DOCUMENTS

| DE | 197 07 970 A1 | 9/1998 |
|---|---|---|
| EP | 0 445 700 A1 | 9/1991 |
| EP | 0 706 790 A1 | 4/1996 |
| EP | 0 751 170 A2 | 1/1997 |
| EP | 0 850 644 A1 | 7/1998 |
| EP | 0 979 643 A2 | 2/2000 |
| FR | 2 765 800 | 1/1999 |
| FR | 2 773 485 | 7/1999 |

OTHER PUBLICATIONS

Abed et al, "Supramolecular association of acid terminated polydimethylsiloxanes", Polymer Bulletin 39, 317–324 (1997).

* cited by examiner

*Primary Examiner*—Sreeni Padmanabhan
*Assistant Examiner*—Gina C. Yu
(74) *Attorney, Agent, or Firm*—Nixon & Vanderhye P.C.

(57) ABSTRACT

The present invention relates to a process for increasing the persistence of at least one cosmetic and/or care effect of a cosmetic composition comprising an oily phase. This process comprises the incorporation into this oily phase of at least one linear or cyclic polyorganosiloxane which comprises at least two organosiloxy units and at least two side and/or end groups which are each capable of forming at least one hydrogen bond with one or more partner groups. The process may be applied, for example, to lipsticks, mascaras or eyeliners to increase the persistence of their coloring effect and/or gloss, to foundations, powders, blushers and eyeshadow to increase the persistence of the matt effect, and to care products such as moisturizing products, deodorants or antiperspirants to increase the persistence of their active care agents. The invention also relates to a cosmetic composition, the persistence of at least one cosmetic and/or care effect of which is increased, and which is intended to be used on the skin, the lips and superficial body growths.

42 Claims, No Drawings

PROCESS FOR INCREASING THE PERSISTENCE OF AT LEAST ONE COSMETIC EFFECT AND/OR CARE EFFECT OF A COSMETIC COMPOSITION, COSMETIC COMPOSITION AND USE THEREOF

The present invention relates to a process for increasing the persistence of at least one cosmetic effect and/or care effect of a cosmetic composition, and to a cosmetic composition, in particular for making up and/or caring for the skin, including the skin of the eyelids, and also of the lips and of superficial body growths such as the eyelashes, the eyebrows, the nails and the hair. The invention also relates to the use of this cosmetic composition as, for example, a lipstick, a mascara, an eyeliner, a foundation, a powder, a blusher, an eyeshadow, a body make-up, a moisturizing product, a deodorant or an antiperspirant.

In cosmetics, it is desired to obtain compositions which, when applied to the skin, the lips and superficial body growths, form deposits, for example film-forming deposits, which have one or more desired special cosmetic and/or care effects.

Thus, for make-up compositions such as lipsticks, mascaras and eyeliners, efforts are made to obtain compositions which form deposits with suitable colouring and/or gloss effects. For compositions including an active care agent such as moisturizing products, deodorants and antiperspirants, efforts are made in particular to obtain the optimal effect of the active care agent present in the composition.

In all cases, efforts are also made to obtain the longest possible duration of the cosmetic and/or care effect(s). For example, for lipsticks, mascaras and eyeliners, it is important to obtain sustained staying power of the colouring effect and/or gloss; for foundations, powders, blushers, eyeshadows and body make-up, it is important to obtain a matt effect which is persistent and durable despite friction or the secretion of sebum or sweat; and for compositions including an active care agent, it is important to obtain the longest possible activity of the active agent.

It has been proposed to incorporate silicone oils into cosmetic compositions. The incorporation of these silicone oils into compositions gives deposits properties of hydrophobicity, gloss and a non-greasy feel, but the deposits obtained show poor resistance to external agents such as sweat or sebum, and in particular to mechanical attack such as friction.

Polysiloxanes comprising amide units and possibly comprising groups capable of establishing hydrogen bonds, which are used as gelling agents for silicone oils in cosmetic compositions, are disclosed in patent WO 99/06473 from Colgate-Palmolive. Compositions that are generally solid, transparent or translucent are thus obtained.

U.S. Pat. No. 5,919,441 from Colgate-Palmolive discloses a cosmetic composition based on a fluid component comprising at least one volatile or non-volatile silicone and at least one gelling agent. This gelling agent is a polymer containing both organosiloxy units and groups forming hydrogen bonds which are chosen from ester, urethane, urea, thiourea and amide groups and combinations thereof. The use of such a gelling agent leads, in particular, to solid compositions, that are preferably transparent or translucent.

Patent FR 2 708 272 from Rhôone-Poulenc discloses the use as adhesives of polyorganosiloxanes comprising groups capable of forming hydrogen bonds.

According to the invention, it has been found that it is possible to increase the persistence of at least one cosmetic and/or care effect of a cosmetic composition comprising an oily phase, by incorporating into the oily phase an effective amount of at least one linear or cyclic polyorganosiloxane comprising at least two organosiloxy units and at least two side and/or end groups each capable of forming at least one hydrogen bond with one or more partner groups.

The expression <<increased persistence of at least one cosmetic and/or care effect of a cosmetic composition according to the invention>> means the fact that at least one cosmetic and/or care effect of the composition (for example the gloss and/or colouring effect for a lipstick, a mascara or an eyeliner, the matt-effect and the staying power of the colour for a foundation, a powder or a body make-up, the suppression of body odours for a deodorant or the moisturization for a moisturizing product) is maintained at its initial level or close to its initial level for a significantly sustained period when compared with a similar composition which does not comprise any polyorganosiloxane containing at least two side and/or end groups each capable of forming at least one hydrogen bond, in particular when exposed to external agents, and more particularly during a mechanical attack such as friction.

According to the invention, the expression <<effective amount of a polyorganosiloxane>> means an amount which is sufficient to significantly increase the persistence of one or more cosmetic and/or care effects of the cosmetic composition.

The term <<partner group>> means any side and/or end group borne by another molecule of the said polyorganosiloxane, which is capable of forming at least one hydrogen bond with the side and/or end group of the said polyorganosiloxane. This partner group may or may not be identical to the side and/or end group with which it forms at least one hydrogen bond.

The term <<oily phase>> means a non-aqueous medium which is liquid at room temperature (25° C.) and at atmospheric pressure ($1.013 \times 10^5$ Pa (760 mm Hg)), containing one or more fatty substances that are liquid at room temperature and under atmospheric pressure, and that are generally miscible with each other.

One subject of the present invention is thus a process for increasing the persistence of at least one cosmetic and/or care effect of a cosmetic composition.

A subject of the present invention is also a cosmetic composition, in particular to make up and/or care for the skin, the lips and superficial body growths such as the eyelashes, the eyebrows, the nails and the hair, which has increased persistence of at least one cosmetic and/or care effect.

Another subject of the present invention is the use of a cosmetic composition according to the invention as a lipstick, mascara, eyeliner, foundation, powder, blusher, eyeshadow, body make-up, moisturizing product, deodorant or antiperspirant. In this case, all these products have at least one cosmetic and/or care effect whose persistence is increased.

Other characteristics, aspects and advantages of the invention will emerge even more clearly on reading the description and the various examples which follow.

One subject of the invention relates to a process for increasing the persistence of at least one cosmetic and/or care effect of a cosmetic composition comprising an oily phase. This process comprises the incorporation into the said oily phase of an effective amount of at least one linear or cyclic polyorganosiloxane comprising at least two organosiloxy units and at least two side and/or end groups each capable of forming at least one hydrogen bond with one or more partner groups.

The polyorganosiloxanes that are suitable in the invention comprise at least two organosiloxy units which may be represented especially by the following formula:

$$R_a R'_b SiO_{(4-a-b)/2} \quad (I)$$

in which:
R represents a linear, branched or cyclic alkyl group, an aryl group, a polyether group or a fluoro group,
R' represents a group capable of forming at least one hydrogen bond, preferably at least two hydrogen bonds,
a is 1, 2 or 3, and
b is 0 or 1, with the proviso that a+b is equal to 2 or 3.

The number of the said organosiloxy units preferably ranges from 2 to 50,000 and better still from 2 to 30,000.

The alkyl groups may be linear, branched or cyclic, and chosen especially from methyl, ethyl, propyl, isopropyl, n-butyl, sec-butyl, tert-butyl, pentyl, cyclopentyl and cyclohexyl groups and other similar groups. The methyl group is particularly preferred.

Among the aryl groups, the phenyl, group is preferred.

Examples of polyether groups which may be mentioned are polyoxyethylene, polyoxypropylene and polyoxyethylene/polyoxypropylene groups.

The fluoro groups may be linear, branched or cyclic alkyl groups, or alkenyl groups, which bear one or more fluorine atoms as substituents.

The groups R' are side and/or end groups capable of forming hydrogen bonds and are preferably chosen from:
(a) groups derived from unprotected or partially protected amino acids, and
(b) carboxylic acid, amine or phenol groups of formula:

—X—(Y)$_n$—Z in which:
X represents a linear, branched or cyclic spacer chain, of alkylene or alkenylene type, optionally comprising one or more hetero atoms in the chain,
Y represents a monocyclic or polycyclic divalent unsaturated hydrocarbon-based group or a divalent unsaturated heterocyclic group, these polycyclic or heterocyclic groups possibly comprising up to 4 fused rings,
n represents an integer ranging from 1 to 4, and
Z represents a —COOH or —OH group or a primary, secondary or tertiary amine group, the nitrogen atom of which optionally forms part of a heterocyclic group Y.

As is well known in the art, a carboxylic acid group may form hydrogen bonds with another carboxylic acid group or an amine group, while an amine group may form hydrogen bonds with a carboxylic acid group or a phenolic OH group.

Thus, it is possible in the process of the invention to use a single polyorganosiloxane containing at least two end and/or side groups, at least one of which is a —COOH group and at least one other of which is a —COOH or amine (primary, secondary or tertiary) group, or alternatively a single polyorganosiloxane containing at least two end and/or side groups, at least one of which is an amine (primary, secondary or tertiary) group and at least one other of which is a phenolic —OH or —COOH group.

Mixtures, preferably equimolar mixtures, of two polyorganosiloxanes comprising partner groups may also be used. Thus, a mixture of a polyorganosiloxane containing at least two —COOH groups with a polyorganosiloxane containing at least two amine groups, or a mixture of a polyorganosiloxane containing at least two amine groups and of a polyorganosiloxane containing at least two phenolic —OH groups, may be used.

The amine and/or carboxylic acid functions in the groups derived from amino acids may be unprotected or partially protected with specific groups such as the acetyl group. Examples of groups derived from amino acids which may be mentioned include cysteine, N-acetylcysteine, glycocoll, alanine and serine, N-acetylcysteine being particularly preferred.

The functionalization of the polyorganosiloxane with these groups derived from amino acids takes place by techniques that are well known to those skilled in the art, such as the silylation of unsaturated bonds with a thiol derivative of the amino acid or by reacting an organohydrogenosiloxane with an amino acid derivative bearing an unsaturated bond.

The spacer chain X is a linear, branched or cyclic alkylene or alkenylene group which may comprise one or more hetero atoms such as N, S or O. Examples of spacer chains which may be mentioned include —(CH$_2$)$_p$—S— and —(CH$_2$)$_p$—O—, p preferably ranging from 1 to 5.

Among the monocyclic or polycyclic divalent unsaturated hydrocarbon-based groups, or unsaturated heterocyclic groups, Y preferably represents a 6-membered aromatic nucleus which may comprise one or more hetero atoms.

Monocyclic or polycyclic divalent unsaturated hydrocarbon-based groups which may be mentioned include phenylene or naphthalene-diyl groups, the phenylene group being particularly preferred.

When Y represents an unsaturated heterocyclic group containing a nitrogen atom, for example, Z may represent an amine group whose nitrogen atom forms part of a heterocyclic group Y and Y—Z is chosen especially from pyridyl, pyrimidinyl and diazanaphthalene-diyl groups.

The polyorganosiloxanes that are suitable in the present invention are linear or cyclic polyorganosiloxanes comprising at least two organosiloxy units and at least two side and/or end groups capable of forming hydrogen bonds, such as those disclosed in the document FR 2 708 272 mentioned above.

The polyorganosiloxanes that are suitable in the invention are used in an amount which is generally in the range from 0.5% to 50% by weight and preferably from 1% to 30% by weight relative to the total weight of the cosmetic composition.

The oily phase which may be used in the process of the invention consists of any cosmetically acceptable oil, chosen especially from oils of mineral, animal, plant or synthetic origin, hydrocarbon-based oils and/or silicone oils, alone or as a mixture provided that they form a homogeneous and stable mixture, and provided that they are compatible with the envisaged use. This oily phase thus comprises at least one hydrocarbon-based oil and/or at least one silicone oil, preferably at least one volatile or non-volatile silicone oil.

The expression <<cosmetically acceptable medium (or oil)>> means a medium (or oil) which is compatible with the skin, the lips and/or superficial body growths, and which also has a pleasant odour, appearance and feel.

The silicone oils may be chosen from polydimethylsiloxanes (PDMSs), that are optionally phenylated, such as phenyltrimethicones, phenyltrimethylsiloxydiphenylsiloxanes, diphenylmethyldimethyltrisiloxanes, diphenyldimethicones, phenyldimethicones and polymethylphenylsiloxanes, optionally substituted with aliphatic and/or aromatic groups, or optionally fluorinated; polysiloxanes modified with fatty acids, fatty alcohols or polyoxyalkylenes, fluorosilicones and perfluorosilicone oils, and mixtures thereof.

Among the silicone oils that are preferred, mention may be made of polydimethylsiloxanes, polymethylphenylsiloxanes, silicones comprising polyoxyalkylene blocks or grafts, in particular polyoxyethylene or copoly(oxyethylene/oxypropylene) blocks or grafts, such as dimethicone copolyols, silicones bearing both hydrophobic hydrocarbon-based groups (for example $C_2$–$C_{30}$ alkyl groups) and polyoxyethylenated or copoly(oxyethylenated/oxypropylenated) blocks or grafts, such as alkyldimethicone copolyols, silicones bearing fluoro or perfluoro groups such as perfluoroalkyl polydimethylsiloxanes and perfluoroalkyl polymethylphenylsiloxanes, and mixtures thereof.

One or more oils that are volatile at room temperature may also be used advantageously. After evaporating off these oils, a supple film-forming deposit is obtained. These volatile oils also make it easier to apply the composition to the skin, the lips and superficial body growths.

The term <<volatile oil>> means an oil which is capable of evaporating at the temperature of the skin or the lips, and which has a non-zero vapour pressure at room temperature and under atmospheric pressure, ranging in particular from 0.13 to $4.0 \times 10^4$ Pa ($10^{-3}$ to 300 mm Hg) and better still greater than 40 Pa (0.3 mm Hg).

These oils may be silicone oils optionally comprising alkyl or alkoxy groups at the end of or pendent on a silicone chain.

As volatile silicone oils which may be used in the invention, mention may be made of linear or cyclic silicones with a viscosity at room temperature and under atmospheric pressure of less than 8 mm$^2$/s (8 cSt) and in particular comprising from 2 to 7 silicon atoms. Mention may be made in particular of octamethylcyclotetrasiloxane, decamethylcyclopentasiloxane, hexadecamethylcyclohexasiloxane, heptamethylhexyltrisiloxane and heptamethyloctyltrisiloxane, and mixtures thereof.

Preferably, at least one volatile silicone oil chosen especially from octamethylcyclotetrasiloxane, decamethylcyclopentasiloxane, hexadecamethylcyclohexasiloxane, heptamethylhexyltrisiloxane, heptamethyloctyltrisiloxane, octamethyltrisiloxane and decamethyltetrasiloxane, and mixtures thereof, may be used.

The term <<hydrocarbon-based oil>> means an oil predominantly containing carbon and hydrogen atoms, and in particular alkyl or alkenyl chains such as alkanes or alkenes, as well as an oil not only containing hydrogen and carbon atoms, but also oxygen atoms, in the form of an ether, ester, alcohol or carboxylic acid function.

Mention may also be made of hydrocarbon-based oils such as liquid paraffin or liquid petroleum jelly, mink oil, turtle oil, soyabean oil, perhydrosqualene, sweet almond oil, beauty-leaf oil, palm oil, grape pip oil, sesame oil, corn oil, parleam oil, arara oil, rapeseed oil, sunflower oil, cottonseed oil, apricot oil, castor oil, avocado oil, jojoba oil, olive oil or cereal germ oil; esters of linoleic acid, of oleic acid, of lauric acid or of stearic acid; fatty esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl) succinate, diisostearyl malate and glyceryl or diglyceryl triisostearate; higher fatty alcohols containing at least 12 carbon atoms, such as stearyl alcohol, oleyl alcohol, linoleyl alcohol, linolenyl alcohol, isostearyl alcohol or octyldodecanol.

In one particular embodiment, the process makes it possible to increase the persistence of the colouring effect and/or gloss of a lipstick by incorporating a polyorganosiloxane as described above into the said oily phase.

The process according to the invention also makes it possible to increase the persistence of the matt-effect and/or colouring effect of foundations, powders, blushers or eyeshadows.

In another embodiment, the persistence of a care effect is obtained with the process of the invention, in particular in the case of moisturizing products, deodorants and antiperspirants. A gelation may be observed as in patents WO 99/06473 and U.S. Pat. No. 5,919,441 from Colgate-Palmolive, which use polysiloxanes that are different from those of the invention, and makes it possible to obtain products which may be used, for example, as deodorants.

Another subject of the present invention is a cosmetic composition for making up and/or caring for the skin, the lips and superficial body growths, the persistence of at least one cosmetic and/or care effect of which is increased. This composition comprises an oily phase comprising at least one volatile or non-volatile silicone oil, into which is incorporated at least one suitable polyorganosiloxane comprising at least two organosiloxy units and at least two side and/or end groups each capable of forming at least one and preferably at least two hydrogen bonds with one or more partner groups.

The said organosiloxy units are represented by formula I above and the said side and/or end groups R' of formula I correspond to the definition given above.

The preparation of the polyorganosiloxanes in the compositions of the invention is known in the art. Preparation examples are disclosed in French patent No. 2 708 272 from Rhône-Poulenc and in the article by S. Abed ed et al., *Polym. Mater. Sci. Eng.,* 1997, No. 76, 45–46.

A first preparation example consists in using a lyorganosiloxane containing unsaturated side groups, ch as vinyl or allylic groups, and in reacting it with sulphanilic derivative such as N-acetylcysteine. A lyorganosiloxane comprising the following units: may thus be obtained.

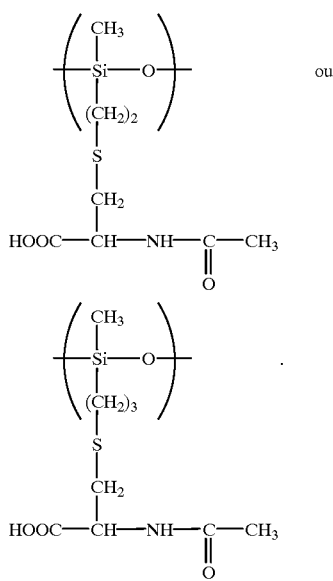

A second preparation example consists in using a polyorganosiloxane containing silyl groups —SiH and in reacting it by hydrosilylation with an amino acid derivative bearing a vinyl or allylic double bond, the carboxylic acid and amine functions of which have been neutralized by silylation, such as, for example:

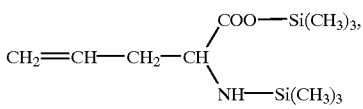

and then, once the hydrosilylation reaction is complete, in deprotecting the carboxylic acid and amine functions. Units of the same type as those represented above are thus obtained.

The synthesis of polyorganosiloxanes containing p-carboxyphenyloxy end groups is disclosed in the article by S. Abed et al., *Polym. Bull.*, 39, 1997, pages 317–324. It consists in first preparing a benzyl p-allyloxybenzoate and in reacting it with a polyorganosiloxane containing —SiH end groups by hydrosilylation. The final step consists in deprotecting the end groups to finally obtain the following product:

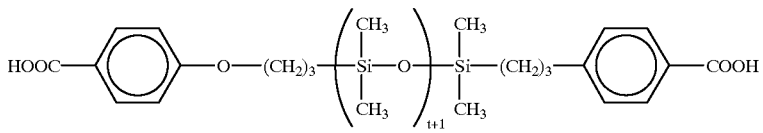

with t preferably ranging from 1 to 1200.

According to the invention, the polyorganosiloxane corresponding to the above formula with t=11 is preferably used.

The oily phase of the cosmetic composition according to the invention preferably comprises at least one volatile or non-volatile silicone oil as described above, and may comprise a hydrocarbon-based oil as mentioned above.

The composition according to the invention may also comprise at least one ingredient chosen from cosmetic active agents and/or active care agents depending on the type of application envisaged, and also various other conventional additives used in cosmetics, such as, for example, fillers, pigments, colourants, surfactants, sunscreens, natural or synthetic waxes, antioxidants, fragrances or preserving agents.

The cosmetic active agents and/or active care agents are used in a proportion that is usual to those skilled in the art, and in particular in a proportion ranging from 0.001% to 30% by weight of the composition.

A person skilled in the art will take care to select the optional additives and the amount thereof such that they do not harm the properties of the compositions of the invention, that is to say they should not be capable of forming hydrogen bonds with the main components of the cosmetic composition, which have been described above.

The fillers may be mineral or organic, and lamellar or spherical. Mention may be made of talc, mica, silica, kaolin, Nylon® (Orgasol® from Atochem) powder, poly-β-alanine powder and polyethylene powder, Teflon®, lauroyllysine, starch, boron nitride, hollow microspheres such as Expancel® (Nobel Industry), Polytrap® (Dow Corning) and silicone resin microbeads (Tospearls® from Toshiba, for example), precipitated calcium carbonate, magnesium carbonate and magnesium hydrocarbonate, hydroxyapatite, hollow silica microspheres (silica beads from Maprecos), glass or ceramic microcapsules, metal soaps derived from organic carboxylic acids containing from 8 to 22 carbon atoms and preferably from 12 to 18 carbon atoms, for example zinc, magnesium or lithium stearate, zinc laurate or magnesium myristate.

The pigments may be white or coloured, and mineral and/or organic. Among the mineral pigments which may be mentioned are titanium dioxide, optionally surface-treated, zirconium oxide or cerium oxide, and iron oxide or chromium oxide, manganese violet, ultramarine blue, chromium hydrate and ferric blue. Among the organic pigments which may be mentioned are carbon black, pigments of D&C type, and lakes based on cochineal carmine or on barium, strontium, calcium or aluminium.

The nacreous pigments may be chosen from white nacreous pigments such as mica coated with titanium oxide or with bismuth oxychloride, coloured nacreous pigments such as titanium mica with iron oxides, titanium mica with, in particular, ferric blue or chromium oxide, titanium mica with an organic pigment of the abovementioned type and nacreous pigments based on bismuth oxychloride.

The liposoluble colorants are, for example, Sudan Red, DC Red 17, DC Green 6, β-carotene, DC Yellow 11 or DC Violet 2. They may represent from 0.01% to 20% of the weight of the composition and better still from 0.1% to 6%.

The surfactants may be anionic, cationic or nonionic surfactants.

The sunscreens are chosen from sunscreens that are active in the UV-A and UV-B range.

For the purposes of the present invention, a wax is a lipophilic compound which is solid at room temperature (about 25° C.), which undergoes a reversible solid/liquid change of state, which has a melting point above about 40° C. and possibly up to 200° C., and which has an anisotropic crystal organization in the solid state. In general, the size of the crystals of the wax is such that the crystals diffract and/or scatter light, giving the composition which comprises them a more or less opaque cloudy appearance. By bringing the wax to its melting point, it is possible to make it miscible with the oils and to form a microscopically homogeneous mixture, but on returning the temperature of the mixture to room temperature, recrystallization of the wax in the oils of the mixture is obtained, which may be detected microscopically and macroscopically (opalescence).

As waxes which may be used according to the invention, mention may be made of waxes of animal origin such as beeswax, spermaceti, lanolin wax and lanolin derivatives; plant waxes such as carnauba wax, candelilla wax, ouricury wax, Japan wax, cocoa butter, cork fibre wax or sugar cane wax; mineral waxes, for example paraffin wax, petroleum jelly wax, lignite wax or microcrystalline waxes or ozokerites; synthetic waxes, including polyethylene waxes, polytetrafluoroethylene waxes and the waxes obtained by Fisher-Tropsch synthesis, or silicone waxes, hydrogenated oils that are solid at 25° C., such as hydrogenated castor oil, hydrogenated jojoba oil, hydrogenated palm oil, hydrogenated tallow or hydrogenated coconut oil, and fatty esters that are solid at 25° C., for instance the $C_{20}$–$C_{40}$ alkyl stearate sold under the tradename <<Kester Wax K82H>> by the company Koster Keunen.

In one particular embodiment of the invention, the compositions according to the invention may be prepared in the usual manner by a person skilled in the art and may be in the form of a cast product, for example in the form of a stick or tube, or in the form of a dish which may be used by direct contact or with the aid of a sponge. In particular, they find an application as cast foundations, cast blushers or eyeshadows, lipsticks, lipcare bases or balms, concealer products, deodorants, antiperspirants, make-up products for the body such as semi-permanent tattoos, antisun products or mascara blocks. They may also be in the form of a soft paste, with a dynamic viscosity at 25° C. of about from 1 to 40 Pa.s, as measured using a Haake RS 50 machine, with a viscosity extrapolated to shear rates of less than 1 s$^{-1}$.

The compositions of the invention are advantageously anhydrous and may contain up to 5% water relative to the total weight of the composition. In this case, they may be in particular in the form of an oily gel, oily liquid or oil, paste or stick. These various forms are prepared according to the usual methods of the fields under consideration.

The compositions of the invention may be used, for example, to increase the persistence of the gloss and/or colouring effect of a lipstick, a mascara, or an eyeliner, to increase the persistence of the matt-effect and/or colouring effect of foundations, powders, blushers, eyeshadows or body make-up such as semi-permanent tattoos, to increase the persistence of the care effects of a moisturizing product or to durably eliminate body odours in the case of a deodorant or an antiperspirant.

The examples which follow illustrate the present invention.

Synthesis of compound A

A polyorganosiloxane containing p-carboxyphenyloxy end groups as defined above is prepared according to the process described in the article by S. ABED, Polymer Bulletin, 39, 317–324 (1997). Compound A of the formula below is thus obtained:

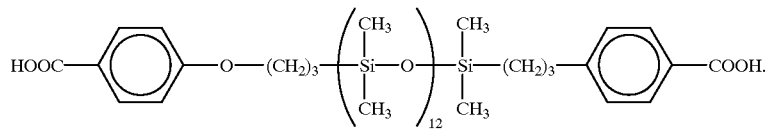

This compound A is used in the examples which follow for the preparation of lipstick and lip gloss.

EXAMPLE 1

A lipstick is prepared having the following composition:

| | |
|---|---|
| Performalene 500 ®[(1)] polyethylene wax | 15 g |
| Compound A | 5 g |
| Pigments | 9 g |
| Hydrogenated polyisobutylene oil[(2)] | 35.5 g |
| Dow 556 Fluid ®[(3)] phenyltrimethicone oil | 35.5 g |

[(1)]sold by the company Petrolite
[(2)]of viscosity 34 mm²/s (34 cSt) at 25° C., sold under the name <<Parleam ®>> by the company Nippon Oil-Fats.
[(3)]sold by the company Dow Corning.

The constituents of the above composition are all mixed together at 110° C. After homogenizing and grinding the pigments, the mixture is cast in a suitable mould. A stick which has good Theological properties is thus obtained. It deposits on the lips a film which has good staying power over time.

EXAMPLE 2

A lip gloss having the composition below is prepared:

| | |
|---|---|
| Compound A | 5 g |
| Pigment (DC Red No. 7 Calcium (lake)) | 5 g |
| Dow 556 Fluid ®(*) phenyltrimethicone oil | 90 g |

(*)sold by the company Dow Corning.

Compound A is first dissolved in the oil. A lip gloss is obtained by dispersing the pigments in this oily phase. The lip gloss thus obtained may be applied to the lips with a brush. It gives a long-lasting, glossy colouring effect.

What is claimed is:
1. Process for increasing the persistence of at least one cosmetic and/or care effect of a cosmetic composition comprising an oily phase, comprising incorporating into the composition of at least one linear or cyclic polyorganosiloxane comprising at least two organosiloxy units and at least two side groups or end groups each capable of forming at least one hydrogen bond with one or more partner groups.

said at least two organosiloxy units being represented by the following formula:

$$R_a\ R'_b SiO_{(4-a-b)/2}$$

in which:
R represents a linear, branched or cyclic alkyl group, an aryl group, a polyether group or a fluoro group,
R' being selected from the group consisting of:
(a) a group derived from an unprotected or a partially protected amino acid, and
(b) a carboxylic acid, an amine or a phenol group of formula:

—X—(Y)$_n$—Z in which:
X represents a linear, branched or cyclic spacer alkylene or alkenylene chain, optionally comprising one or more hetero atoms in the chain,
Y represents a monocyclic or polycyclic divalent unsaturated hydrocarbon-based group or a divalent unsaturated heterocyclic group, these polycyclic or heterocyclic groups optionally comprising up to 4 fused rings,
n represents an integer ranging from 1 to 4, and
Z represents a —COOH or —OH group or a primary, secondary or teriary amine group,
a is 1, 2 or 3, and
b is 0 or 1, with the proviso that a+b is equal to 2 or 3.
2. Process according to claim 1 wherein the polyorganosiloxane comprises from 2 to 50,000 organosiloxy units.
3. Process according to claim 1, wherein the side and/or end groups are each capable of forming at least two hydrogen bonds with one or more partner groups.
4. Process according to claim 1, wherein Y represents a 6-membered aromatic nucleus and Z represents a —COOH group.

5. Process according to claim 4, wherein the polyorganosiloxane is represented by the following formula:

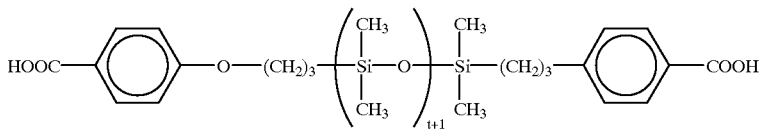

with t ranging from 1 to 1200.

6. Process according to claim 5, wherein the polyorganosiloxane is represented by the following formula:

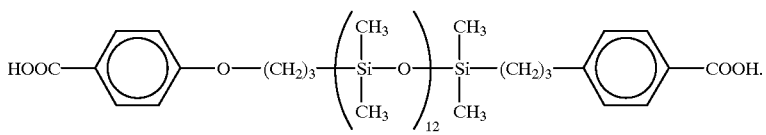

7. Process according to claim 1, wherein the effective amount of the polyorganosiloxane is between 0.5% and 50% by weight relative to the total weight of the cosmetic composition.

8. Process according to claim 7, wherein the effective amount of the polyorganosiloxane is between 1% and 30% by weight relative to the total weight of the cosmetic composition.

9. Process according to claim 1, wherein the oily phase comprises at least one hydrocarbon-based oil and/or at least one silicone oil.

10. Process according to claim 9, wherein the oily phase contains at least one volatile or non-volatile silicone oil.

11. Process according to claim 9, wherein the silicone oil is selected from the group consisting of polydimethylsiloxanes (PDMSs), that are optionally phenylated; polymethylphenylsiloxanes, optionally substituted with aliphatic and/or aromatic groups, or optionally fluorinated; polysiloxanes modified with fatty acids, fatty alcohols or polyoxyalkylenes; perfluorosilicone oils.

12. Process according to claim 11, wherein the silicone oil is selected from the group sonsisting of polydimethylsiloxanes, polymethylphenylsiloxanes, silicones comprising polyoxyalkylene blocks or grafts, silicones bearing both hydrophobic hydrocarbon-based groups and polyoxyethylenated or copoly(oxyethylenated/oxypropylenated) blocks or grafts, and silicones bearing fluoro or perfluoro groups.

13. Process according to claim 1, wherein said polyorganosiloxane increases the persistence of the colouring effect and/or gloss of a lipstick, a mascara or an eyeliner.

14. Process according to claim 1, wherein said polyorganosiloxane increases the persistence of the matt-effect and/or colouring effect of foundations, powders, blushers, eyeshadows or body make-up.

15. Process according to claim 1, wherein said polyorganosiloxane increases the persistence of an active care agent for moisturizing products, deodorants or antiperspirants.

16. Cosmetic composition comprising an oily phase which comprises at least one volatile or non-volatile silicone oil, to which is added an effective amount of at least one linear or cyclic polyorganosiloxane comprising at least two organosiloxy units and at least two side groups or end groups which are each capable of forming at least one hydrogen bond with one or more partner groups, wherein said organosiloxy units are represented by the following formula:

$$R_a R'_b SiO_{(4-a-b)/2}$$

in which:

R represents a linear, branched or cyclic alkyl group, an aryl group, a polyether group or a fluoro group, R' represents a group capable of forming at least one hydrogen bond, a is 1, 2 or 3, and b is 0 or 1, with the proviso that a+b is equal to 2 or 3, R' represents:

(a) a group derived from unprotected or partially protected amino acid, and (b) carboxylic acid, amine or phenol groups of formula:

$$-X-(Y)_n-Z$$

in which:

X represents a linear, branched or cyclic spacer alkylene or alkenylene chain, optionally comprising one or more hetero atoms in the chain, Y represents a monocyclic or polycyclic divalent unsaturated hydrocarbon-based group or a divalent unsaturated heterocyclic group, these polycyclic or heterocyclic groups possibly comprising up to 4 fused rings, n represents an integer ranging from 1 to 4, and Z represents a —COOH or —OH group or a primary, secondary or tertiary amine group.

17. Cosmetic composition according to claim 16, wherein the polyorganosiloxane comprises from 2 to 50,000 organosiloxy units.

18. Cosmetic composition according to claim 16, wherein the side groups or end groups are each capable of forming at least two hydrogen bonds with one or more partner groups.

19. Cosmetic composition according to claim 16, wherein Y represents a 6-membered aromatic nucleus and Z represents a —COOH group.

20. Cosmetic composition according to claim 19, wherein the polyorganosiloxane is represented by the following formula:

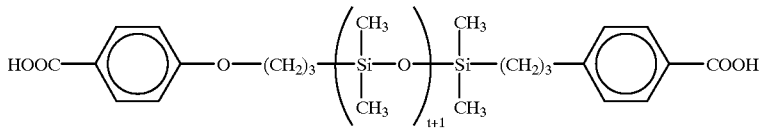

with t preferably ranging from 1 to 1200.

21. Cosmetic composition according to claim 20, wherein the polyorganosiloxane is represented by the following formula:

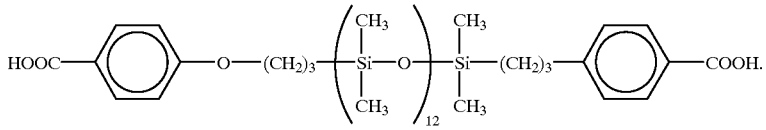

22. Cosmetic composition according to claim 16 wherein the effective amount of the polyorganosiloxane is between 0.5% and 50% by weight relative to the total weight of the cosmetic composition.

23. Cosmetic composition according to claim 22, wherein the effective amount of the polyorganosiloxane is between 1% and 30% by weight relative to the total weight of the cosmetic composition.

24. Cosmetic composition according to claim 16, wherein the oily phase also comprises at least one hydrocarbon-based oil.

25. Cosmetic composition according to claim 16, wherein the silicone oil is selected from the group consisting of polydimethylsiloxanes (PDMSs), that are optionally phenylated; polymethylphenylsiloxanes, optionally substituted with aliphatic and/or aromatic groups, or optionally fluorinated; polysiloxanes modified with fatty acids, fatty alcohols or polyoxyalkylenes, fluorosilicones and perfluorosilicone oils.

26. Cosmetic composition according to claim 25, wherein the silicone oil is selected from the group consisting of polydimethylsiloxanes, polymethylphenylsiloxanes, silicones comprising polyoxyalkylene blocks or grafts, silicones bearing both hydrophobic hydrocarbon-based groups and polyoxyethylenated or copoly(oxyethylenated/oxypropylenated) blocks or grafts, and silicones bearing fluoro or perfluoro groups.

27. Cosmetic composition according to claim 16, further comprising at least one of a filler, a pigment, a colorant, a surfactant, a sunscreen, a natural wax, a synthetic wax, an anti-oxidant, a fragrance and a preserving agent.

28. Cosmetic composition according to claim 16, wherein said composition is anhydrous.

29. Cosmetic composition according to claim 16, in the form of a stick, a tube, in the form of a soft paste, with a dynamic viscosity at 25° C. of about from 1 to 40 Pa.s, in the form of a dish, an oily gel or an oily liquid.

30. A method of making up and or caring for the skin comprising applying a composition of claim 16 to said skin.

31. Cosmetic composition according to claim 16, in the form of a lipstick, a mascara, an eyeliner, a foundation, a powder, a blusher, an eyeshadow or a body make-up.

32. Cosmetic composition according to claim 16, in the form of a moisturizing product, a deodorant or an antiperspirant.

33. A process according to claim 1, wherein incorporating said polyorganosiloxane increases the persistence of the colouring effect and/or gloss of a lipstick, a mascara or an eyeliner.

34. A process according to claim 1, wherein incorporating said polyorganosiloxane increases the persistence of the matt effect and/or colouring effect of a foundation, a powder, a blusher, an eyeshadow or a body make-up.

35. A process according to claim 1, wherein incorporating said polyorganosiloxane increases the persistence of the care effect of a moisturizing product.

36. (Amended) Cosmetic composition according to claim 16, in the form of a deodorant or an antiperspirant.

37. A process according to claim 2 wherein said polyorganosiloxane comprises from 2 to 30,000 organosiloxy units.

38. A process of claim 11 wherein the silicone oil is selected from the group consisting of a phenyltrimethicone, a phenyltrimethyl siloxydiphenylsiloxane, a diphenylmethyldimethyltrisiloxane, a diphenyldimethicone, and a phenyldimethicone.

39. A process according to claim 12 wherein said polyoxyalkylene blocks or grafts are polyoxyethylene or copoly(oxyethylene/oxypropylene) block or grafts, said hydrocarbon-based groups are $C_2$–$C_{30}$ groups, said polyoxyethylenated or copoly(oxyethylenated/oxypropylenated) blocks or grafts are alkyldimethicone copolyols, and said silicones bearing pertluoro groups are perfluroroalkyl polydimethylsiloxanes or perfluoroalkyl polymethylphenylsiloxanes.

40. A composition of claim 17 wherein said polyorganosiloxane comprises from 2 to 30,000 organosiloxy units.

41. A composition of claim 26 wherein said polyoxyalkylene blocks or grafts are polyoxyethylene or copoly(oxyethylene/oxypropylene) block or grafts, said hydrocarbon-based groups are $C_2$–$C_{30}$ groups, said polyoxyethylenated or copoly(oxyethylenated/oxypropylenated) blocks or grafts are alkyldimethicone copolyols, and said silicones bearing perfluoro groups are perfluoroalkyl polydimethylsiloxanes or perfluoroalkyl polymethylphenylsiloxanes.

42. A method of claim 30 wherein said skin is eyelids, lips or nails.

* * * * *